United States Patent [19]
Doherty et al.

[11] Patent Number: 5,904,296
[45] Date of Patent: *May 18, 1999

[54] APPARATUS AND SYSTEM FOR SYNCHRONIZED APPLICATION OF ONE OR MORE MATERIALS TO A SURFACE FROM A VEHICLE AND CONTROL OF A VEHICLE MOUNTED VARIABLE POSITIONS SNOW REMOVAL DEVICE

[75] Inventors: John A. Doherty, 829 St. Andrews La., Louisville, Colo. 80027; Charles A. Kalbfleisch, Boulder, Colo.

[73] Assignee: John A. Doherty, Louisville, Colo.

[21] Appl. No.: 08/879,921

[22] Filed: Jun. 20, 1997

Related U.S. Application Data

[63] Continuation-in-part of application No. 08/783,556, Jan. 14, 1997, which is a continuation of application No. 08/660,232, Jun. 7, 1996, Pat. No. 5,619,193

[60] Provisional application No. 60/020,237, Jun. 21, 1996, and provisional application No. 60/031,036, Nov. 18, 1996.

[51] Int. Cl.$^6$ ................................................ B05B 7/00
[52] U.S. Cl. .......................... 239/61; 239/69; 239/663; 239/665; 239/675; 701/50
[58] Field of Search .................................. 239/172, 656, 239/662, 663, 665, 668, 675, 681, 687, 1, 677, 684, 61, 62, 63, 71, 69; 222/608, 626; 701/50; 702/FOR 135

[56] References Cited

U.S. PATENT DOCUMENTS

| | | | |
|---|---|---|---|
| 3,160,964 | 12/1964 | Boyer et al. | 239/684 X |
| 3,519,169 | 7/1970 | Holland | 222/626 |
| 3,995,569 | 12/1976 | Picardat | 239/656 X |
| 4,442,979 | 4/1984 | Kupper | 239/656 |
| 4,491,275 | 1/1985 | Holsworth | 239/687 X |
| 4,588,127 | 5/1986 | Ehrat | 239/662 X |
| 5,069,392 | 12/1991 | Wise et al. | 239/675 |
| 5,096,125 | 3/1992 | Wise et al. | 239/675 |
| 5,186,396 | 2/1993 | Wise et al. | 239/675 |
| 5,267,696 | 12/1993 | Balmer | 239/662 |
| 5,318,226 | 6/1994 | Kime et al. | 239/687 X |
| 5,515,623 | 5/1996 | Weeks | 239/289 X |
| 5,619,193 | 4/1997 | Doherty et al. | 340/905 |
| 5,653,389 | 8/1997 | Henderson et al. | 239/172 X |

OTHER PUBLICATIONS

Advertisement, Root Snow Plows.
Mobile GPS Builds On 7400 Technology To Claim The Future of Pavement Management,,FactsFinder.
Advertisement, Henderson Manufacturing Reversible Plow.
Advertisement, Henderson Manufacturing Patrol Wing.
Advertisement, Tenco Side Wings.
Advertisement, Tenco Reversible Plow.
Surveyors Use Pedal Power to Map City, ENR, Nov. 13, 1995.
Trimble, AEC Automation Newsletter, Sep. 1995.
GPS Satellites, Trimble Precise Positioning Systems.
GPS Goes Real Time, Civil Engineering, Sep. 1994.

*Primary Examiner*—Andres Kashnikow
*Assistant Examiner*—Steven J. Ganey
*Attorney, Agent, or Firm*—John R. Wahl; Holland & Hart LLP

[57] ABSTRACT

An apparatus and system, preferably mounted on a service vehicle, provides synchronized application of fluid materials, either solid or liquid, to a vehicle travel surface in proportional amounts or spatially distributed proportions in response to user defined requirements and/or operation of a vehicle mounted component in response to conditions encountered in real time. A first embodiment is a vehicle mounted apparatus and system for coordinated application of a plurality of materials to a surface simultaneously and in desired proportions and/or widths automatically and/or selectively. A second embodiment includes a granular material distribution device and includes a plurality of liquid spray headers and pumping, means. A third embodiment of the present invention is a vehicle mounted apparatus and system for automated coordinated application of a plurality of materials to a surface as well as automated component control such as blade blocking plate control based on sensed current surface condition information and current accurate location information as well as past operating history and predicted near term weather conditions.

25 Claims, 10 Drawing Sheets

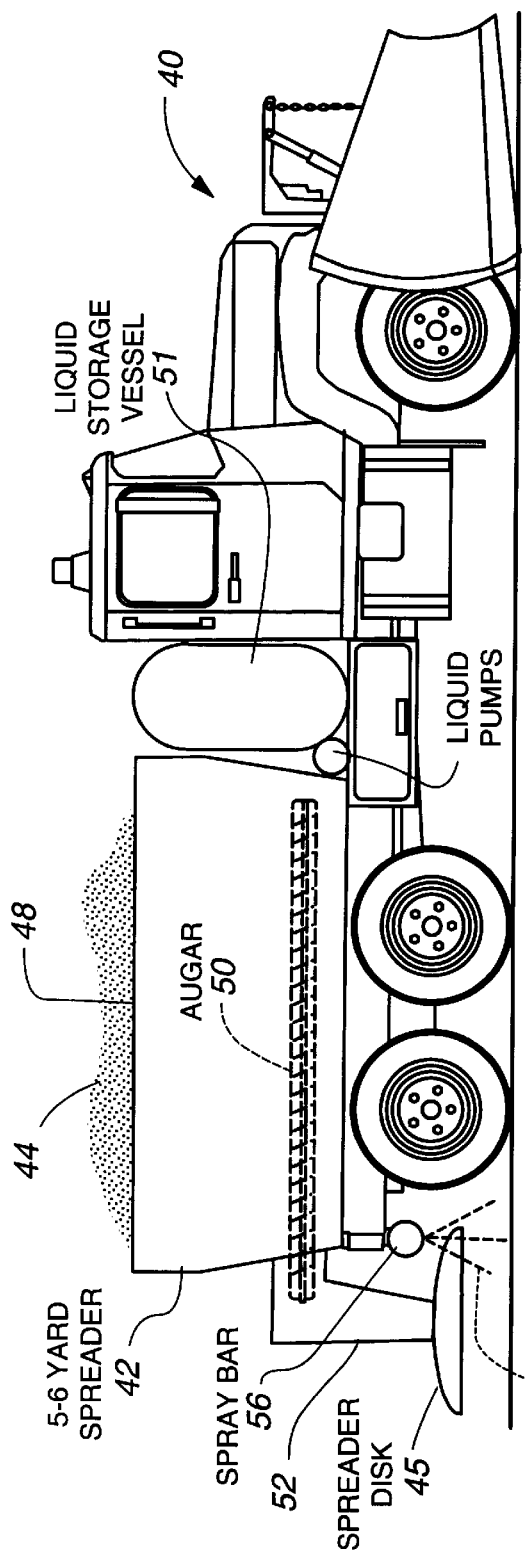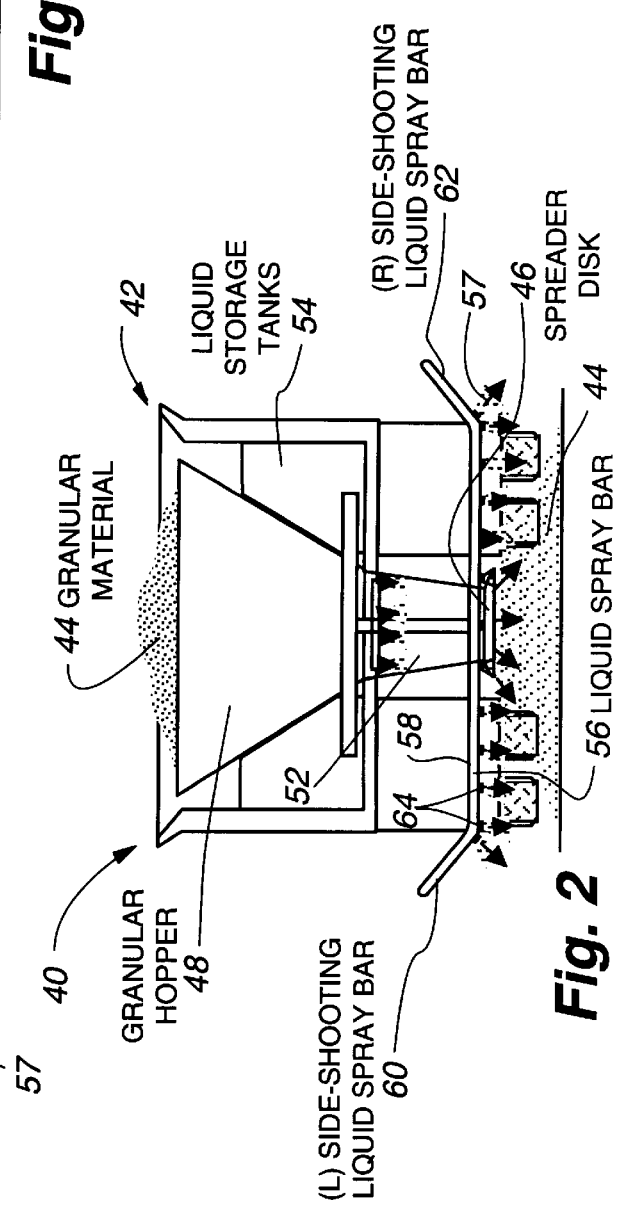

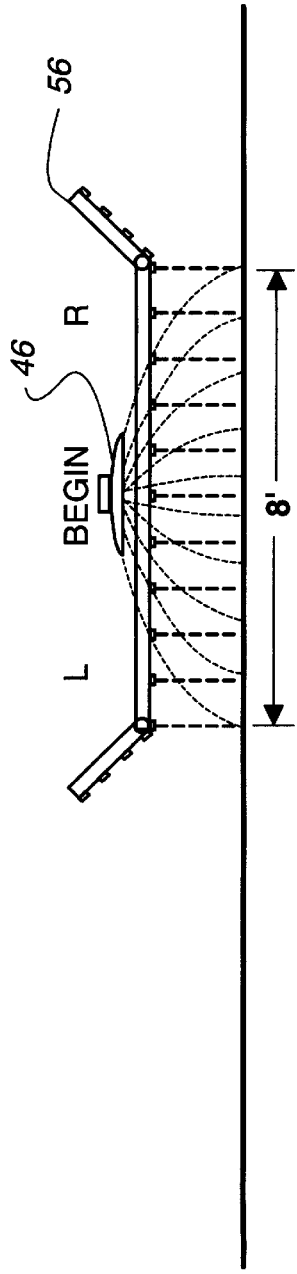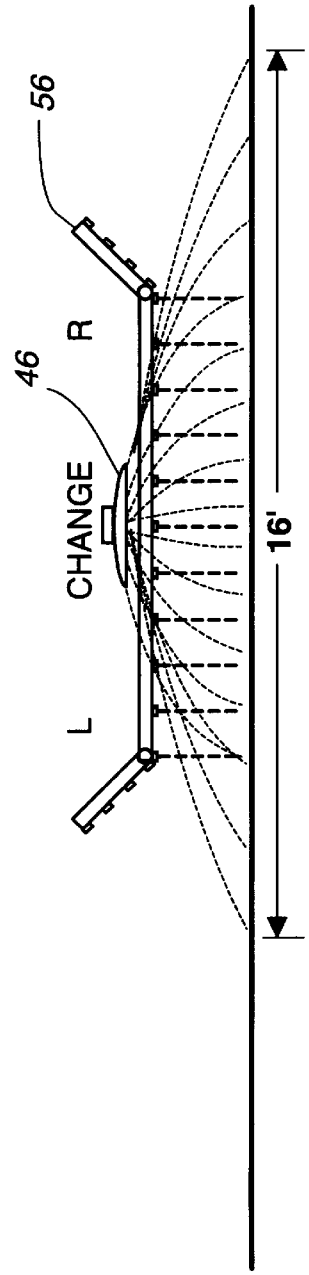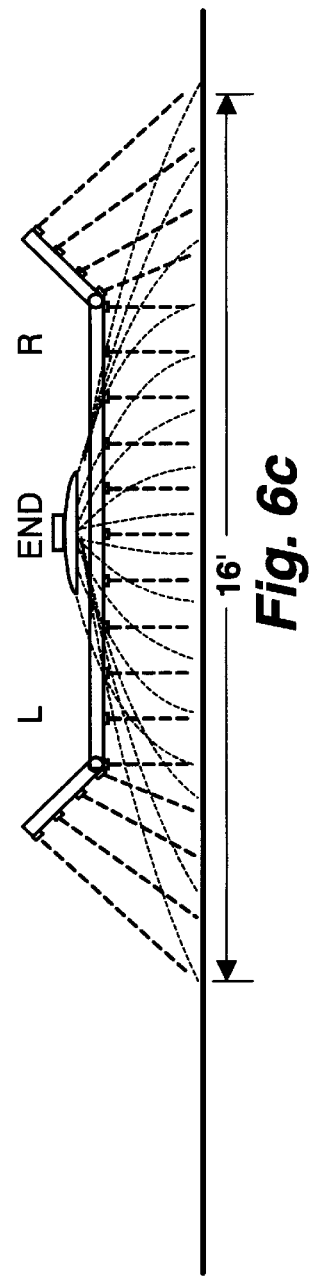

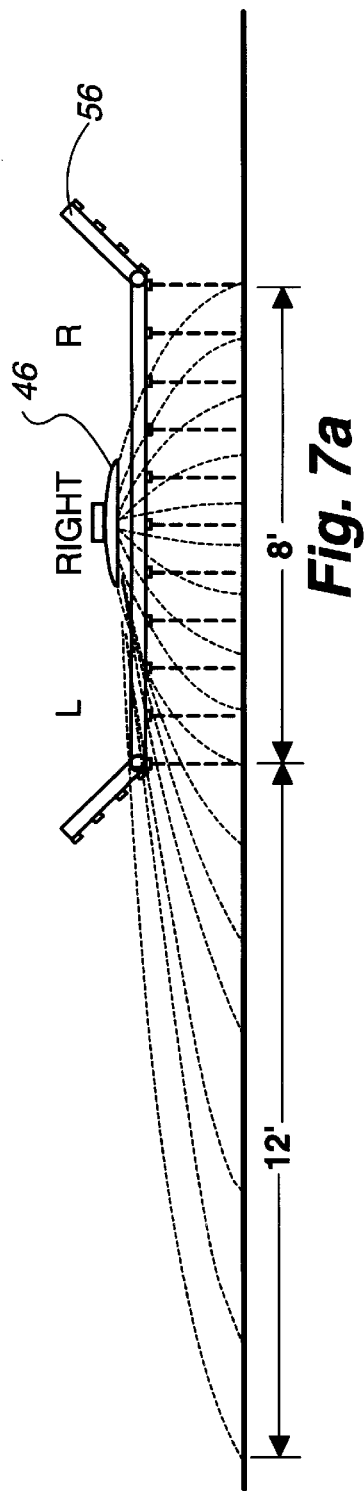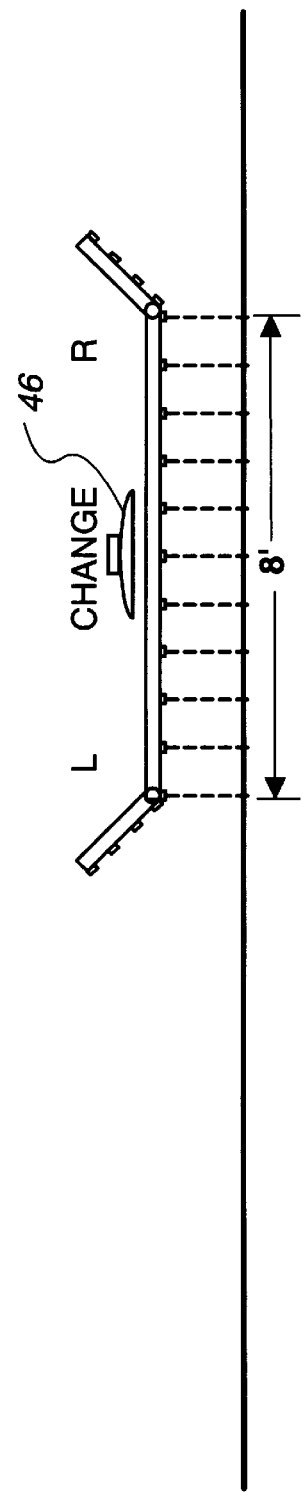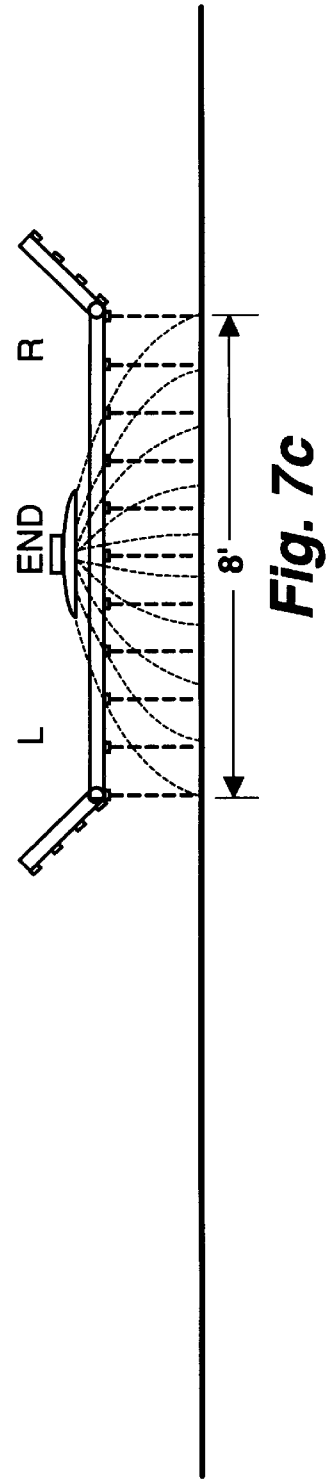

APPARATUS AND SYSTEM FOR SYNCHRONIZED APPLICATION OF ONE OR MORE MATERIALS TO A SURFACE FROM A VEHICLE AND CONTROL OF A VEHICLE MOUNTED VARIABLE POSITIONS SNOW REMOVAL DEVICE

CROSS REFERENCE TO RELATED APPLICATIONS

This application is a continuation-in-part of U.S. patent application Ser. No. 08/783,556, filed Jan. 14, 1997, which is a continuation of application Ser. No. 08/660,232, filed Jun. 7, 1996 and now U.S. Pat. No. 5,619,193. This application also claims the benefit of U.S. Provisional Patent Application Ser. Nos. 60/020,237, filed Jun. 21, 1996 and 60/031,036, filed Nov. 18, 1996.

BACKGROUND OF THE INVENTION

1. Field of the Invention

This invention relates generally to surface conditioning vehicles such as those carrying material spreaders and/or snow removal devices, and more particularly relates to a new and improved apparatus for synchronized material spreading which indexes certain characteristics of a material delivery system such as the spread width of at least a second material in response to a change in the width of spread of a first, or triggering, material and automated control of surface conditioning equipment based on actual surface conditions.

2. Description of the Related Art

Surface conditioning vehicles include material spreaders that are used in many applications. For example, they may be used to provide pesticide and fertilizer spreaders in agricultural applications, as well as vehicles for the control of ice and snow on roadways and may include snow plows, blowers, and material spreaders, alone or in combination. In either of these general applications, often it is desirable to spread more than one material simultaneously in either a synchronous or asynchronous manner in either a predetermined ratio or in random proportions to a surface.

The materials to be applied to a surface can be all liquids, all solids, or combinations thereof. Generally, these materials can be referred to materials A & B. The widths of the plurality of materials are manually controlled independently such that the user must decrease or increase the spread-width for each material separately.

For example, in a pre-wetting arrangement, both liquid and granular materials are typically dispersed by a common device such as a spinner disk. In this example, the quantity of liquid is small compared to the amount of granular material. Because of material characteristics, such as density, viscosity, granularity, and flowability, and desired driveability results it is sometimes advantageous to have a separate delivery system for each material. This liquid and granular combination also helps control the bounce and scatter of the granular materials.

In spreading materials on roadways and runways for the control of ice and snow, oftentimes both granular and liquid material are desired to be spread simultaneously. In many instances, each material has its own delivery system. The operator sets the spread-width of the granular material and the spread-width of the liquid material independently of one another. In the event the width of the road changes, or the operator changes the width of spread for any of a variety of reasons, such as allowing a vehicle to pass, the operator must separately act to reduce the spread-width of the granular material and the spread-width of the liquid material.

The problem with the conventional material spreading systems resides in the difficulty in accurately adjusting the spread-width of each material, in addition to the time and attention it takes for the operator to modify the spread-width while driving the vehicle.

A similar problem exists for operators of surface conditioning vehicles which include snow plows and snow blowers, especially in residential areas. During heavy snow conditions, the conventional plows push the snow aside to one side or the other and thus can create a substantial pile of snow in front of driveways. This pile is often compacted and difficult to remove. A recent solution to this problem has been to equip the vehicle with at least one hydraulically actuated discharge blocking plate on at least one of the ends of the snow blade. The vehicle operator may raise and lower these plates to close off the blade discharge path as the plow passes driveways or other features where snow discharge is undesirable. The drawback of this arrangement is that the system is manually controlled and thus requires constant operator vigilance and action to lower and raise the blocking plates.

It is against this background that the significant improvements and advancement of the present invention have taken place in the field of surface conditioning vehicles, and particularly material spreaders and snow removal controls.

SUMMARY OF THE INVENTION

The present invention comprises an apparatus mounted on a service vehicle for synchronized application of fluid materials, either solid or liquid, to a surface such as a runway or roadway in proportional amounts or spatially distributed proportions in response to user defined requirements and/or operation of a vehicle mounted component in response to conditions encountered in real time.

A first embodiment of the present invention is a vehicle mounted apparatus and system for coordinated application of a plurality of materials to a surface simultaneously and in desired proportions and/or widths automatically and/or selectively.

A second embodiment of the present invention is a vehicle mounted apparatus and system for coordinated application of a plurality of materials to a surface simultaneously and in desired proportions and/or widths automatically and/or selectively. The apparatus includes a granular material distribution device and includes a plurality of liquid spray headers and pumping means.

A third embodiment of the present invention is a vehicle mounted apparatus and system for automated coordinated application of a plurality of materials to a surface as well as automated component control such as blade blocking plate control based on sensed current surface condition information and current accurate location information, preferably in conjunction with learned weather and surface conditions.

The first embodiment of the present invention comprises a vehicle mounted apparatus for dispensing one or more materials to a surface such as a roadway. The apparatus includes a control box and distribution means for coordinated dispensing one or more fluid materials (the slave material) in response to the dispensing rate or pattern of another fluid material (the triggering material). The fluid materials may be solids such as sand or salt granules or liquids of various types. The apparatus preferably includes a liquid supply tank, pump, and application spray header and a solid fluid material storage container or hopper, auger, and distribution means such as a spinner disk, and a control box operably connected to the pump and spray header, the spinner disk, and the auger motor.

The second embodiment of the present invention is similar to the first except that the system further includes a second spray bar for pre-wetting the granular material prior to the granular material being dispensed.

The third embodiment of the present invention incorporates an on board system for sensing and analyzing actual road surface conditions at the vehicle location and utilizes an on board computer and database to selectively manually or automatically control the application of spreader materials and/or certain operations of a vehicle preferably equipped with a snow plow or blower. The third embodiment includes Global Positioning System receivers and computer controlled reporting capabilities to update other mobile or stationary stations as well as permit the on board computer to receive current and store historical environmental condition data in a Geographical Information System format in order to automatically adjust material application compositions and rates to optimally condition the road surface and control snow plow or blower configurations.

BRIEF DESCRIPTION OF THE DRAWINGS

FIG. 1 is a side view of a spreader vehicle incorporating the synchronized-width material spreader in accordance with a first embodiment of the present invention.

FIG. 2 is a rear-end view of a second embodiment of a vehicle including the synchronized-width material spreader of the present invention, illustrating a granular hopper, liquid storage tanks, spreader disk, and two liquid spray bars, one for pre-wetting and one for direct application.

FIG. 6 is a schematic representing the operation of the synchronized-width material spreader, and illustrates an increase in the width of material spread using the synchronized-width material spreader of the present invention.

FIG. 7 is a schematic of the operation of the synchronized-width material spreader illustrating a decrease in the width of material spread.

DETAILED DESCRIPTION OF THE INVENTION

Figure 3:
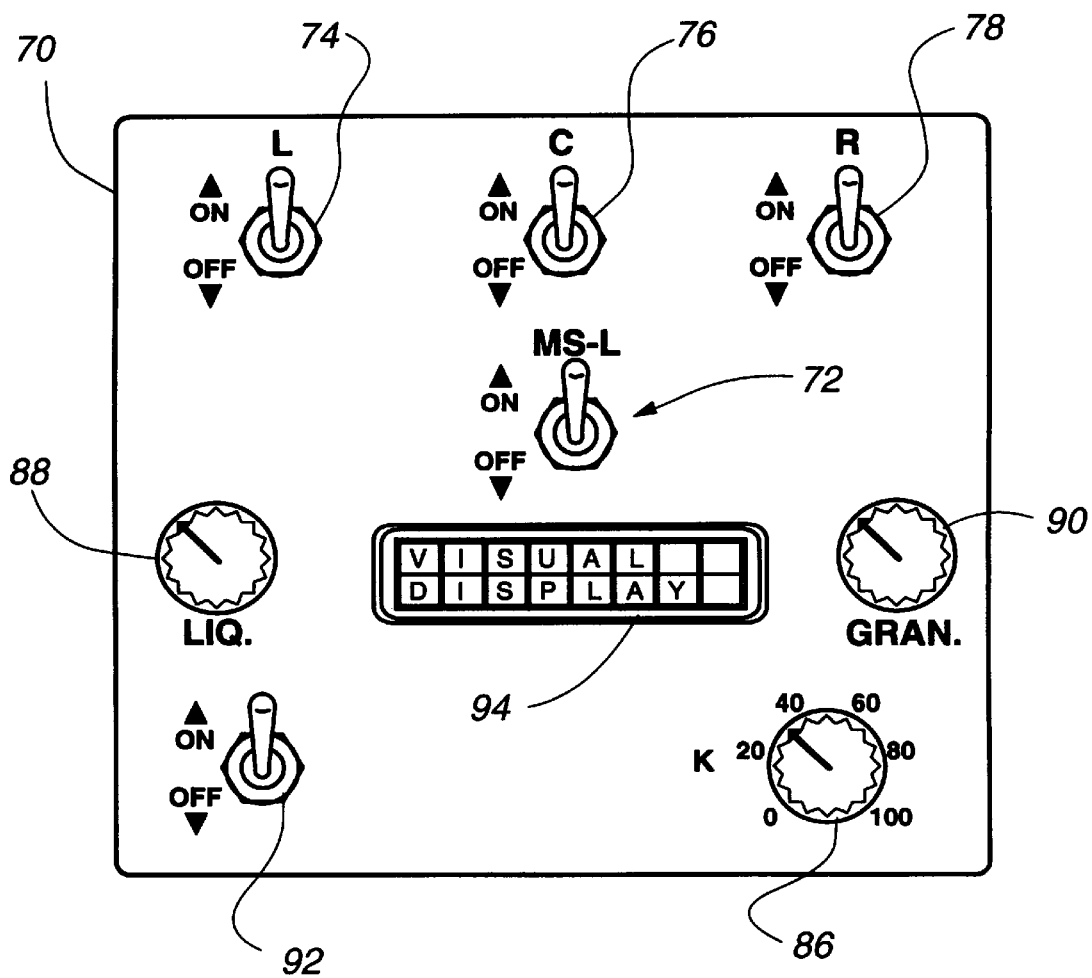
FIG. 3 is a first embodiment of a control box for use in controlling the synchronized-width material spreader in accordance with the invention.

Referring to FIG. 1, a snow plow vehicle 40 incorporating the synchronized-width material spreader system 42 in accordance with a first embodiment of the present invention is shown. The snow plow vehicle 40 includes a system for storing and spreading granular material, as well as a system for storing and spreading liquid material. While the vehicle could include multiple systems for storing and dispensing several individual types of fluid materials, for the purposes of clarity, the description herein is based on a vehicle having the capability of storing and dispensing only two different materials. In this particular example, there is one granular fluid material and one liquid fluid material. It is to be understood that there may be more than two materials as well as any combination of granular and/or liquid materials.

Further, the synchronized-width material spreader of the present invention as described in this specification is used in the environment of controlling snow and ice on roadways for descriptive purposes only. The invention is applicable to many different uses, such as for crop fertilizing, ground conditioning during road construction, etc. It is to be understood that the synchronized spreader may equally well be utilized for these and other purposes where the distribution of two or more similar or dissimilar materials is desired.

The granular material 44 is typically dispensed from the truck 40 by use of a spinning disk 46, but may also be dispensed by other means such as gravity or air pressure. The granular material 44 is typically a granular chemical or abrasive material. The granular material 44 stored in the hopper 48 is conveyed, such as by an auger 50 to a chute 52 at the rear of the truck through which it falls into contact with the spinning spreader disk 46. In this example, the spreader disk 46 spins about its center generally vertical axis and imparts a tangential force to the granular material as it falls onto the disk. The granular material is spread or spewn over a path width, which is determined in part by the speed of rotation of the spreader disk 46, and many other parameters, such as density of the material.

Rotation of the spreader disk 46 may be caused by any of a variety of means, including an electric motor, air pressure, or hydraulic pressure. Other dispensing mechanisms may also be used in place of the spreader disk 46. For example, two rotating belts that trap the material and sling it out behind the truck could also be used. Alternatively, the material could be propelled from the storage hopper or container out through an orifice via air pressure or through venturi action, for example. Any of such dispensing mechanisms may be used in the present invention.

The width of spread of the granular material 44, or liquid material 57, is measured in a direction transverse to the length of the vehicle 40, and is typically analogous to the width dimension of a road, upon which the vehicle 40 travels. For instance, in FIG. 2, the spreader disk 46 may deliver granular material in a path having an arc width equal to the width of the vehicle 40. The material can also be projected rearwardly (to facilitate a lower or zero-velocity impact with the ground), forwardly, or at any angle from the truck.

The liquid dispensing system utilized in the present invention may comprise a liquid storage vessel 54 positioned on the vehicle 40 behind the cab of the vehicle, in front of the hopper 48, as shown in FIG. 1. Alternatively, the liquid storage vessel 54 may essentially be bifurcated and positioned along the length of the vehicle on the outer sides of the granular hopper, as is shown in FIG. 2. Many other liquid tank positions could be utilized or the tanks could form part of the structural portion of the granular hopper 48 or a structural portion of the vehicle 40.

A spray bar 56 preferably extends laterally at the rear end of the vehicle 40 and is generally adjacent to the spreader disk 46, as is shown in FIG. 1. The spray bar 56 may also be formed by a vertical stack of smaller spray bars and nozzles. The spray bar 56 preferably may have side shooting extensions 60 and 62 attached at its opposite ends to allow liquid 57 to be sprayed at a greater width through the spray bar. The liquid spray 56 bar position may also be locally or remotely variable so that it may extend at any angle from the truck, to create any number of orientations. For example, the spray bar may be vertically oriented for spraying roadside vegetation or shoulder areas. FIGS. 1 and 2 illustrate a typical preferred transverse spray bar position for a flat road surface.

Liquid is preferably conveyed from the liquid storage vessel 54 to the spray bar 56 through conventional piping by means such as a positive displacement or centrifugal liquid pump which pumps the liquid material from the storage vessel to the spray bar, or by pressure means such as selectively pressurizing the liquid storage vessel itself, or by gravity feed, which would force the liquid through the piping to the spray bar 56.

In the preferred example illustrated in FIG. 2, the spray bar has a center portion 58 and two preferably remotely movable side spraying portions 60, 62. The spray bar 56 is essentially a tube which has nozzles or apertures 64 formed therein to allow the liquid flowing through the spray bar 56 to spray onto the road surface. The side spraying extensions 60, 62 are preferably rotatably attached at either end of the spray bar central portion 58 and are in fluid communication with the center portion 58 of the spray bar 56 in all positions when a single central pump is utilized. When separate pumps are utilized, the central portion 58 need not be in fluid communication with the end portions 60 and 62.

A series of remotely operable baffles or valves such as solenoid valves are positioned within the spray bar 56 adjacent to or as part of each nozzle 64 to facilitate changing the width of spray emanating from the spray bar 56. The width of spray can be controlled by either the operator or by automated control. The valves or flow restrictors such as baffles can optionally be placed at discreet positions along the length of the spray bar 56, and include positions in the left or right end portions 60, 62 of the spray bar 56. The valves, flow restrictors or baffles or other flow control devices could also be made to operably move along the length of the liquid spray bar 56 to provide virtually infinite width control.

The spread distance or spray path width of the liquid dispensing system for a given type of material depends upon the orientation of spray bar and/or nozzles, and both the pressure at which the liquid is forced through the pipe system and into the spray bar 56, and the selective activation of the valves or baffles found on or inside the spray bar 56. Typically the spray bar 56 receives fluid from the center piping connection such that any width control mechanism is necessarily positioned along the length of the spray bar relative to the location of the connection between the piping system and the spray bar.

The liquid can alternatively also be spread by means of a rotating disk (not shown), in which case the spray bar or set of spray bars are replaced with at least one rotating nozzle disk or set of disks, and the spread width of the liquid thus depends on the disk orientation and placement and speed of the rotating disk in an analogous fashion to the rotating disk 46 used with the granular material as well as the discharge pressure and orifice size. Other means of spreading the liquid material may also be utilized such as through a selectable set of variable orifice discharge nozzles and/or flow control valves mounted on the truck.

For ease of description in this specification, the center of the spread-width for the granular material 44 and the center of the spread-width for the liquid material 57 are positioned co-extensively with one another at the rear of the vehicle 40.

In general, the synchronized-width material spreader works, either manually or optionally automatically, to control the spread-width and direction of the second or nth material based on the change of spread-width of the trigger or first material. For instance, if the trigger or first material is the granular material 44 being spread at a predetermined rate, when the spread-width of the granular material increases by 50%, the synchronized-width material spreader system automatically increases the spread-width of the liquid material 57 by a predetermined percentage, in this example, 50%, to match the increased spread-width of the granular material 44. Likewise, if the granular material 44 decreases in spread-width by 50%, the synchronized-width material spreader system automatically decreases the spread-width of the liquid material 57 by 50%.

A user selectable pre-set ratio selected from a range of ratios can also be maintained. For instance, if the liquid material spread width is selected to be two-thirds (66%) of the granular material spread width, then when the trigger material spread width is changed, either increased or decreased, the spread width of the other, or "slave" material is also chanced to maintain the pre-selected ratio.

Also, a sliding scale or trigger/slave distribution arrangement based on a mathematical relationship may be used, e.g. based on certain characteristics of the multiple materials may be deployed such as, if trigger material spread width is "x" feet, then slave material would be "y" — for example 50% of x feet. This configuration may be desirable to compensate for differences in particle sizes, density, liquid viscosity, atomization particle sizes, bounce, etc. Therefore, as the trigger width changes from minimum to maximum, the slave material width, due to above mentioned characteristics could be varied, say, from 40% to 70% of trigger material spread-width. As another example, if the sliding scale ratio is 0.33, and the granular material spread width is increased by 6 feet, the liquid material is increased by only 2 feet (33%). Likewise, if the granular material spread width is decreased by 3 feet, the liquid material spread width is likewise decreased by 1 foot (33%). This capability is particularly useful where the trigger material may have one particle size and the slave may have a different particle size or mass, resulting in different roadway bouncing characteristics between the two materials, in order to have a desired uniform or non-uniform pattern of deposition on the roadway surface. This capability may also be advantageously employed when particle weight, particle size, density, liquid viscosity, atomization sizing, etc. behave differently, yielding other than uniform distributions when direct proportioning is utilized.

Such a sliding scale can also be implemented, whereby the change of the slave or following material (liquid in example above) is only increased or decreased a set percentage or fraction of the change in the trigger or primary material (granular material in example above). Again, the ratio of slinging, propelling force could also change if the trigger was being sent, for example, 10 ft verses 50 ft. to achieve the same result. The change in material distribution may also be based on vehicle location, etc. For instance, the material distribution may be different for steep hills than on flat level roadway surfaces.

Using this inventive proportioning system of the invention, the operator can simply control, for example, the spread-width of each of the different materials being dispensed onto the road surface by controlling one trigger material or by having the width of the first material automatically changed based on vehicle location. Consequently, the operator need only actuate the width control system for the trigger material, and the operator does not have to separately and independently control the spread-width of the second or additional or nth material unless special circumstances warrant such control as it will automatically follow the trigger in accordance with the preset or preprogrammed proportions.

The synchronized-width material spreader apparatus is beneficial in many circumstances, such as where the roadway narrows, and the width of spread of the various materials must be adjusted to a chosen value for an extended period of time, and also where the width of spread need only be temporarily adjusted, such as where at least a second vehicle or obstacle passes relatively alongside the spreader vehicle 40.

For instance, automated control could be triggered by a stationary signal device adjacent to, in or on the roadway as part of an Intelligent Transportation System (ITS). Additionally, by use of Geographic Information System (GIS) data in conjunction with Global Positioning System (GPS) data, the precise vehicle location may be automatically determined and automated control initiated. The particular ratio, or scaling, between the spread widths can also be maintained, as described below.

A preferred methodology involves a control system having a microprocessor and associated software that can control the material spreader to distribute both materials in such a fashion that a width-change in one material is driven by and/or sensed by the microprocessor, which then initiates a change in the drive mechanism for the width of the other, or second material (more than two materials could be controlled) so that the proportioning or width of both materials is synchronized and/or adjusted even though the materials leave their separate and distinct launching and/or propelling devices and travel through the air before landing on the road surface.

Other methods for coordinating a change in the width of one material with a like or predetermined (such as for scaling or ratios) change in the width of a second or nth material might include, singularly or in any combination, the following:

1. The synchronization/coordination in width of spread could be accomplished with electrical control devices such as relays or solid state switches in such a fashion that a change in one relay conditioned with the triggering material would initiate a change in a different relay coordinated with the second, or nth material that would increase or decrease the width of spread of the second or nth material by affecting the propelling means of the other second material or materials.
2. The change in the width of the second material could be implemented through the use of hydraulically actuated devices since the spreader disk, for example is typically operated by a hydraulic motor. The control hydraulic pressure in the trigger material delivery system could be sensed or utilized by the control system to thereby control, i.e. effect a change in the width of spread of the other material.
3. Optionally, the change of width could be accomplished with pneumatic air power in a manner similar to 2 above.

If only one material is being dispensed from the vehicle 40, obviously there would be no need for width coordination for the other materials. However, control of the application width is still very desirable in many circumstances. The application width of the one material may be controlled manually via the control box 70 or automatically in response to ITS sensor or GPS signals or other sensory devices placed in, on, or near the roadway in order to optimally distribute the material to the roadway surface without over-dispensing or under-dispensing the material being deposited.

A proximity sensor can be utilized to control the synchronized-width material spreader system on the vehicle 40. The proximity sensors of any known type, such as radar or optical, may be ground based, sub-surface based, aerial based, or vehicle mounted, and can be used from any location, either stationary or truck mounted, to detect the presence of the subject vehicle, or of an oncoming, approaching, or passing vehicle or stationary obstacle, and act through operable connection to the control system to modify the spread width and/or proportionality of the various materials. GPS signals may also be used in order to precisely fix the location of the vehicle 40 and compare previously stored environmental condition data at the vehicle's location with current conditions as is described more fully below.

The proximity sensor, if mounted on the truck, can be positioned at a variety of locations, most notably the front and rear of the vehicle, to sense the presence of oncoming and passing vehicles. As noted above, the proximity sensor or signal receiver can also be positioned in or on the ground, in the air or other location remote from the truck to send signals to the truck with the same result.

In addition, the global positioning system (GPS) receiver signal can be used as an input to the automatic control of the material spread width as well as for adjusting various material types and amounts, etc. being applied through the use of the control system. For instance, if the course on which the truck 40 is traveling has been determined and mapped in GIS format and stored in a computer database, for the optimal spread widths and material proportionality at different geographical features or locations, such as, without limitation, bridges and locations of differing road widths, then the control system can be triggered by the real-time GPS readings to adjust the spread width to the known optimal dimensions, deposit desired material types and amounts, etc at the appropriate locations.

While the synchronized-width material spreader 42 is described herein in use on a spreader system having a different dispensing system for each of the two different materials, the synchronized-width material spreader system can also be used and implemented with a spreader having a common launching mechanism, which is capable of differential launching speeds based on differing characteristics of the multiple materials so that both or all materials travel the desired distance. In this case, differential distances (absolute or percentages) would be selected according to the characteristics of the materials and the optimal dispensed mixture rates. Spreader system 42 can also be used in spreaders dispensing several different materials. Different materials will travel different distances with the same throwing power. Therefore, a calibration of the launching mechanism coupled with the various materials to be utilized will help increase the accuracy of the spread width.

As another example where the ratio of spread widths is 1.5:1 between, for instance, but not limited to, granular and liquid materials, the granular (trigger) material would be spread at a distance of 9 feet, and the liquid would be spread at a distance of 6 feet. If the control system is actuated to reduce the spread width of the granular material to 6 feet, the liquid spread width would automatically be reduced to 4 feet to maintain the ratio to 1.5:1 between the granular and liquid spread widths. Alternatively, the spreader control system could allow the ratios to be reversed or adjusted as desired by the operator, other person, or automatically.

Referring to FIG. 3, a first embodiment of a control box 70 for use with the synchronized-width material spreader system 42 shown in FIGS. 1 and 2 is shown. The control box 70 can be positioned adjacent the operator in the truck or integrated into the dashboard of the vehicle, and can be used by the operator to simply control the material or materials being dispensed from the vehicle, either manually or automatically. Alternatively, the control box could be at a position remote from the driver, or even the truck, to operate a slave unit and could be controlled by a third party or controller device, thus requiring the driver to simply drive, while the material dispensing system 42 is controlled by a third party or remote computer via the slave unit mounted in the vehicle.

The first and second embodiments of the invention, shown in FIGS. 1 and 2, contemplate controlling two materials a granular material 44 and a liquid material 57, with the granular and liquid systems being analogous to those previously explained and described above. The same or a similar system, as described herein, could also be used to control more than two materials, whether they be liquids or granular materials and in any combination. The control box 70 in the embodiment shown in FIG. 3 contains a plurality of toggle switches 72, 74, 76, 78. and 92 as well as a plurality of fine-adjustment knobs 86, 88, and 90, each having a specific use. Master switch 72 is the master switch for the liquid spreading system. When the master switch 72 for the liquid spreading system is turned on, the liquid material control switches 74, 76 and 78 are enabled and can be operated. The toggle switch 74 is an on/off actuation switch device for controlling the liquid flowing through the left end 60 of the liquid spray bar 56, which is controlled by an associated left liquid valve 80 (shown schematically in FIG. 8). Once activated, the valve 80 could be proportionately controlled by the control box 70, as described further below. Switch 76 is an on/off toggle switch similar to switch 74, but instead is used to actuate the flow of liquid material through the center portion 58 of the liquid spray bar 56, and controls the center liquid valve 82 in the liquid dispensation system (see FIG. 8). Once activated, the valve 82 can be proportionately controlled by the control box 70. The switch 78 is an on/off toggle switch for actuating the flow of liquid through the right portion 62 of the liquid spray bar 56, and controls the right liquid valve 84 (see FIG. 8). Once activated, the valve 84 could be proportionately controlled by the control box 70. The position of the knob 86 controls the speed of rotation of the disk 46 which spreads the granular material 44 and is graduated between zero and 100% dry material spread-width. The control knob 88 controls the rate of flow of liquid through the liquid dispensing system (for instance, in gallons per lane mile). The control knob 90 controls the rate of granular material being dispensed through the granular dispensing system (for instance pounds of material per lane mile). The ON/OFF master switch 92 controls the on/off status of the entire spreader system. The visual display screen 94 is used to indicate to the operator what the settings are.

In using the first embodiment of the control box as disclosed in FIG. 3, the granular material 44 is the trigger material from which the system triggers the liquid spread-width. The operator first turns on the spreader system by toggling the ON/OFF master switch 92 to ON. The operator then sets the rate of granular disbursement and the rate of liquid disbursement using the appropriate control knobs 88, 90, respectively. At this point, the operator is only engaging the dispensing system for dispensation of liquid material to the road surface. The switches 74, 76 and 78 are appropriately activated by the operator as desired. As shown in FIG. 3, all three switches are in the ON position. This results in liquid 57 being dispensed from the entire spray bar 56 through the left, center and right portions.

In operation, where the first embodiment of the control box shown in FIG. 3 is used, and the granular material 44 is considered as the trigger material off of which the spread width of the slave liquid material 57 is controlled, the operator modifies the width of the granular spread by adjusting the control knob K. Adjusting the K control knob causes a signal to be sent through the electrical lines to the disk valve 150 to allow more hydraulic fluid to flow through the motor 144 for the disk 46. Adjusting the granular knob 90 in turn causes a signal to be sent through the electrical lines to the auger valve 148 and allows more or less hydraulic fluid to flow through the motor 142 for the auger thus changing the rate at which the granular material is fed to the disk 46. This in turn changes the speed at which a disk spins, thus changing the granular spread width. As discussed, the change in granular width using the K control knob will be sensed and cause a change in liquid spray width.

Control knob 86 is shown positioned at approximately 30% of the maximum disk speed, to control the granular material spread-width. In this situation, both granular 44 and pre-wetting liquid 57 materials are being spread by the disk 46, and the liquid material being spread by the spray bar. In the event that control knob 86 is rotated to 75% of maximum granular spread-width, software internal to the control box 70 controls the increase in disk 46 spinning speed, causing the granular material 44 to be spread to a greater width. Software internal to Box 70 simultaneously senses the selected increase in the granular spread-width and accordingly sends sufficient liquid material to the center, left and right spray bar portions 58, 60 and 62 to match the new width of the granular material being disbursed by the disk 46.

The nozzles 64 in the spray bar 56 can also be adjusted accordingly by the software controller to adjust their spread-widths appropriately. The operator can also shut down the left, right or center portions of the spray bar 56 and keep them from dispensing liquid 57 there through by operating the toggle switches 74, 76 or 78, respectively, manually. This would be effective for temporarily turning off, for instance, the liquid disbursement from the left spray bar portion 60 to allow an oncoming vehicle to pass the vehicle 40. In this example, if the liquid was the trigger material, this action would also typically automatically adjust the width of the nth material.

Figure 4:
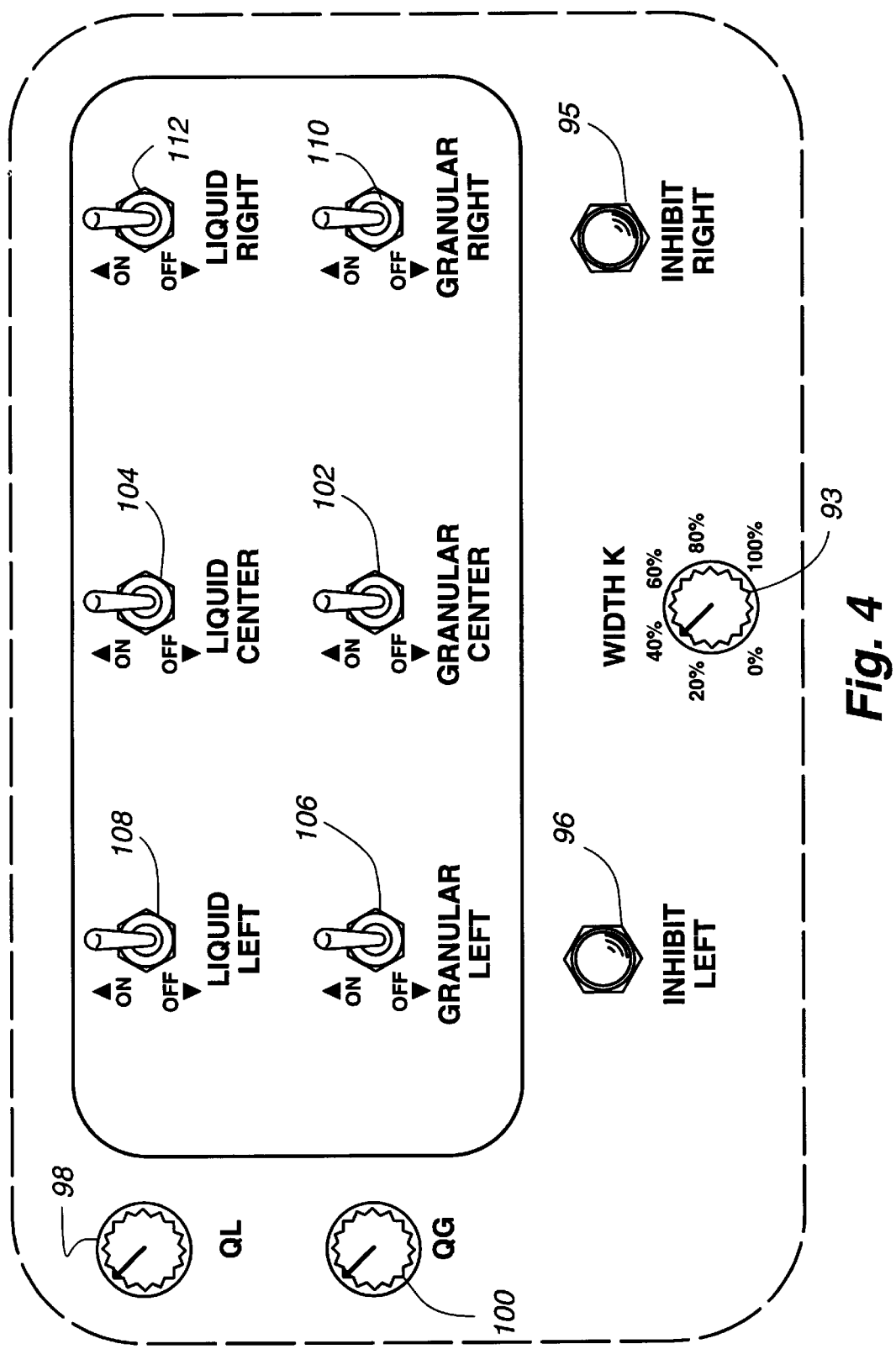
FIG. 4 is a second embodiment of a control box for controlling the operation of the synchronized-width material spreader in accordance with the invention.

Turning now to FIG. 4, with the granular material 44 as the trigger material, a second embodiment of the control box 91 is disclosed. The control knob 93 controls the width of spread of any and all materials which are enabled. The Inhibit right control knob 95 will inhibit any enabled material from being spread to the right side of the carrier regardless of the spread-width selected on control knob 93. The control knob 98 controls the rate of liquid disbursement through the spray bar 56 to the road surface (for instance gallons per lane mile). The control knob 100 controls the rate of granular material 44 disbursement to the road surface (for instance pounds per lane mile). The granular material dispensing means and the liquid material dispensing means are controlled by each appropriate switch: center 102, 104; left 106, 108; and right 110, 112 on the control box 91. These switches allow the operator to selectively turn on and off as desired the spread of material in any of these regions.

Figure 5:
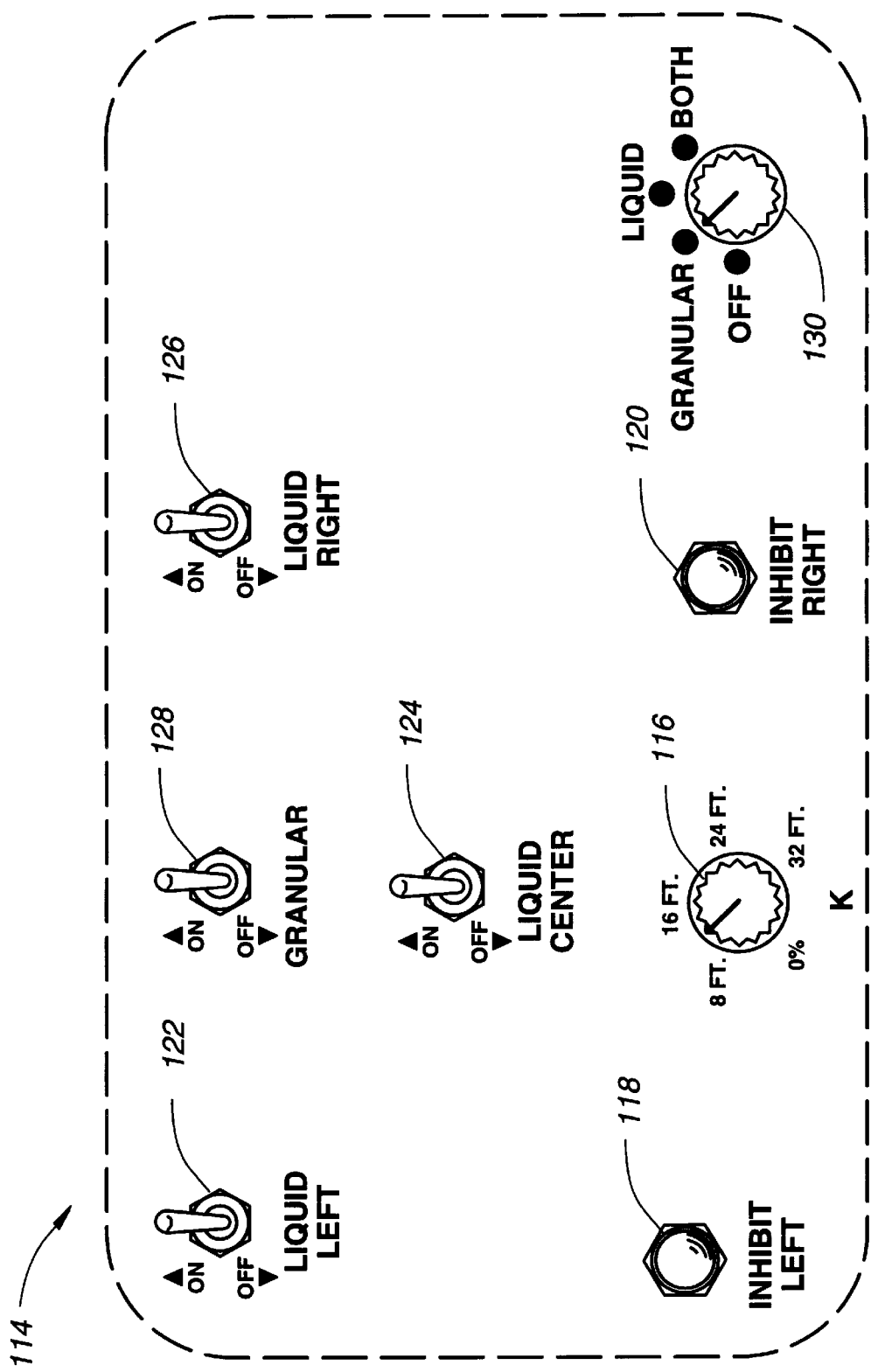
FIG. 5 is a third embodiment of a control box for use in operating the synchronized-width material spreader.

Turning now to FIG. 5, a third embodiment of control box 114 is disclosed. The third embodiment of the control box includes a control knob 116 which controls the width of spread of any enabled materials, and an Inhibit Left control knob 118 and Inhibit Right control knob 120, a left 122, center 124 and right 126 liquid on/off toggle switch, and a single granular on/off toggle switch 128. A master control switch 130 allows the operator to turn the dispensing system on for granular material spreading only, liquid material spreading only, or a combination of granular and liquid material spreading.

As an example of the general operation of the synchronized-width material spreader, FIG. 6 discloses an increase in the spread-width of the liquid disbursement triggered by the increase of the granular spread-width. The synchronized-width material spreader system thus causes the liquid spread-width to automatically control the width of the granular spread-width. In FIG. 6A, the granular material is shown as being spread to a width of approximately eight feet by the spread disk, and the liquid is being spread to a width of approximately eight feet by the center portion of the liquid spray bar. In FIG. 6B the operator increases the granular material spread-width to 16 feet by appropriately modifying the K control knob setting, for instance in the first embodiment of the control box 70. The synchronized-width material spreader system 42, through the various sensing means employed therein, senses the increase in the spread-width of the granular material, and automatically increases the spread-width of the liquid material through the spray bar portions, in this instance by actuating the left and right portions of the liquid spray bar, which causes the liquid spread-width to match the granular spread width (FIG. 6C).

In FIG. 7, a decrease in the spread-width of the granular material, as triggered by the decrease in spread-width of the liquid material is shown. In FIG. 7A the spread-width of both the granular and liquid material is set at approximately 20 feet. The operator then actuates the control of the liquid disbursement to reduce the liquid spread-width to approximately eight feet without use of the side extension nozzles as shown in FIG. 7b. (FIG. 7b is shown without the granular material distribution illustrated for clarity). The synchronized-width material spreader system, through the various sensor means employed therein accordingly reduces the spread-width of the granular material by, for instance, reducing the spin speed of the disk (FIG. 7c).

The width and direction of material spread off of a spinning disk 46 can be controlled by the point of impact of the granular material 44 as it strikes the disk 46. As is well known, if the disk 46 is moved with respect to the dispensing chute, or the chute is moved with respect to the spinning disk 46 so that the impact point is changed radially and/or circumferentially around the disk, the desired flow width and direction can be controlled.

Figure 8:
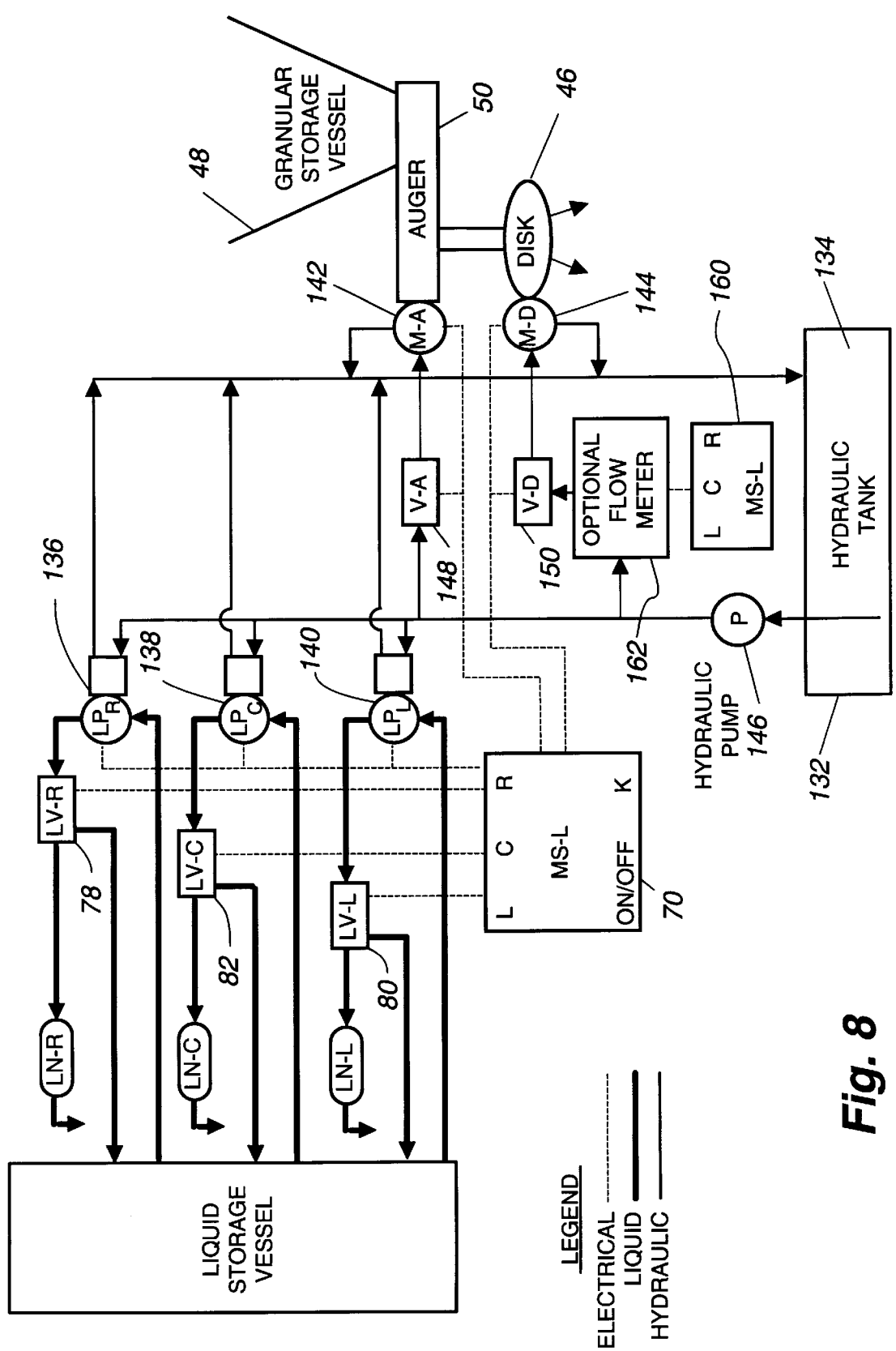
FIG. 8 is a schematic of the hydraulic, electrical and material flow system utilized in operation of the synchronized-width material spreader.

Referring now to FIG. 8, a schematic diagram of the hydraulic fluid, liquid material and electrical control system is disclosed. The hydraulic system is a closed-loop system and comprises a hydraulic fluid reservoir 132 which provides a source for the hydraulic fluid 134 in the system and a repository for the return hydraulic fluid. The hydraulic fluid system controls the power setting on the various hydraulically driven liquid pumps 136, 138 and 140, which control the amount of fluid flow through the nozzles as ultimately controlled by the operator through the control box. The hydraulic system also controls the power setting of the motor for the auger 142 which drives the auger 50 to move the granular material 44 to the disk 46, as well as the motor 144 driving the disk, which controls the spin speed of the disk, which ultimately controls the spread-width of the granular material 44. The hydraulic fluid flows through the various lines under pressure generated by the pump 146 and flows through the various liquid pumps as necessary, and recirculates to the hydraulic tank reservoir 132. The hydraulic fluid flows through the various lines under the pressure of the pump 146 to the motor for the auger 142 and the motor 144 for the disk, as determined by the settings on the control box 70. The hydraulic fluid also flows through the valves 148, 150 for the auger motor and the disk motor, respectively, the values being controlled by the control box 70 settings, and recirculates through a return line to the hydraulic reservoir 132.

The liquid material system includes a liquid storage reservoir 152, which stores the liquid for dispensing through the spray bar, a plurality of liquid lines connected from the storage reservoir 152 to communicate and be acted upon by the appropriate pump, such as LP,, through a dedicated liquid valve 84 in line with the liquid material 57, at which point the liquid is diverted either back to the liquid storage reservoir, or to the liquid nozzle 158. Each of the left, center and right portions of the liquid spray bar have an associated pump, valve, and nozzle arranged as previously described. Alternatively, there could just be one liquid pump in the system. With only one pump in the system, appropriately controlled valves and sensors would provide feedback to control the liquid pump output volume to compensate for changes in demand based on user controlled valve operations and corresponding width of spread.

The electrical system is controlled by the control box (for instance, box 70) and communicates to the liquid valves for the left, center and right portions of the liquid spray bar, the liquid pumps 140, 138, and 136 associated with the left, center and right liquid spray bar portions (if separate pumps are provided), the valve 148 for the auger and the valve 150 for the disk, which control the hydraulic fluid flow to the motor auger 142 and the motor disk 144, respectively. The motor auger MA drives the auger to move the granular material to the spinning disk, the motor MD drives the spinning disk 46.

The optional flow meter 162 is designed to feed information regarding disk speed to a controller 160 which controls the liquid spray width. The liquid spray width is preferably varied by controller 160 as a result of sensing more or less hydraulic fluid flow from the pump 146 to the granular launching device for the trigger material, such as the spinner disk 46.

The software of the synchronized width material spreader system 42 senses the increase in spread width of the granular material 44 and sends the appropriate signal to the liquid valves and liquid pumps for each of the right center and left portions of the liquid boom 56 and allows more hydraulic fluid to drive the liquid pumps to pump the fluid through the boom at a higher pressure. The liquid valves, such as LV-R, also are opened or adjusted accordingly to allow the liquid to flow at the appropriate rate and proportion through the valve and to the nozzle to accordingly increase the width of spread of the liquid dispensing. The liquid valves control the amount of liquid material 57 that flows back to the liquid storage reservoir 132 or to the nozzles on the spray bar 56, and when in combination with the increased pressure generated by the liquid pump can cause the liquid material to be sprayed over a greater width. The nozzles could also be adjustable to provide even a finer control of the liquid material spread-width. Reducing the spread-width of the liquid material as triggered by the granular material spread-width operates analogously. Of course, the spread-width of the granular material can be controlled as a slave with a trigger being the spread-width of the liquid material.

Figure 9:
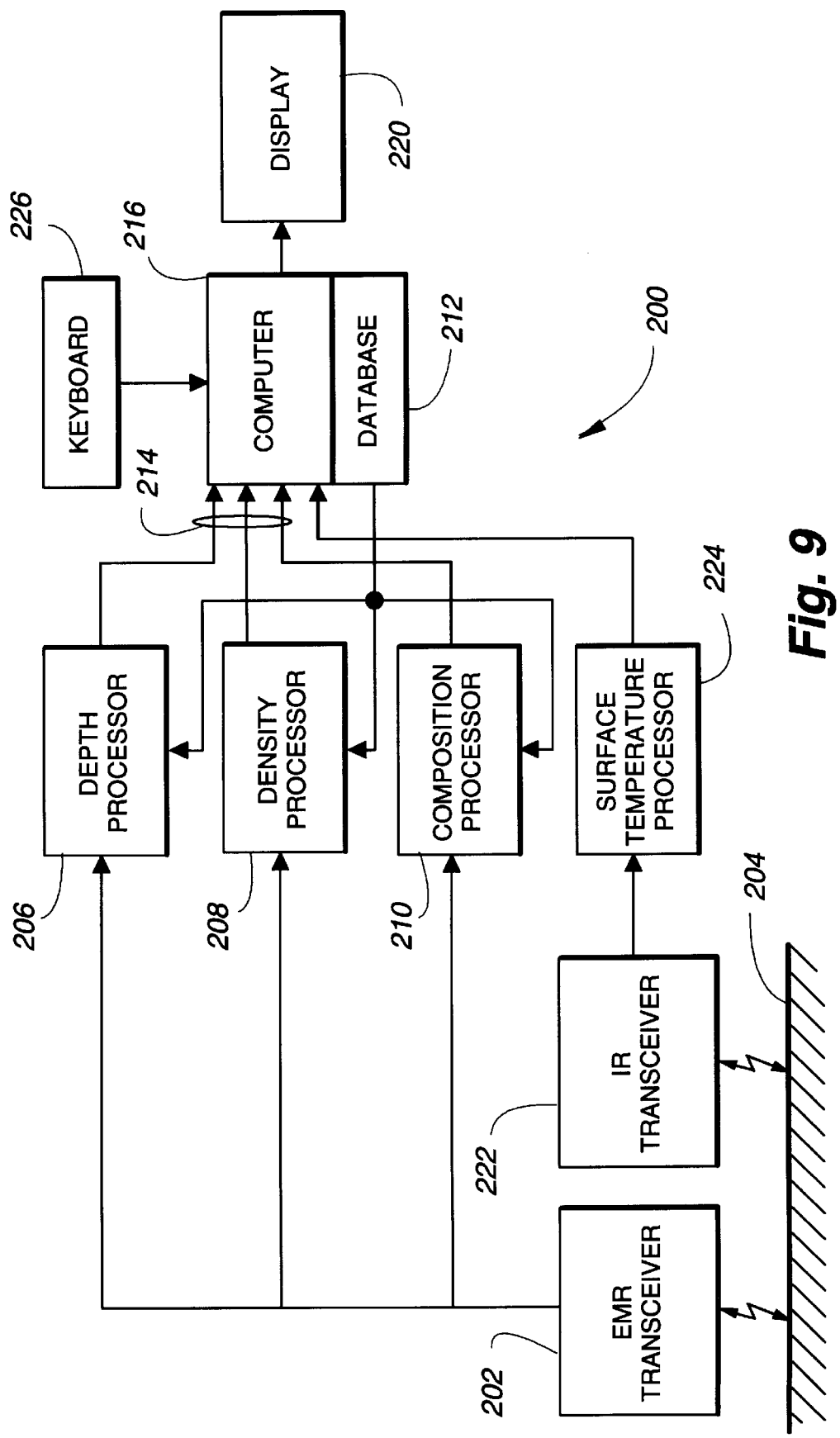
FIG. 9 is a block diagram of a remote sensing system incorporated into an automatic control system in a third embodiment of the invention.
Figure 10:
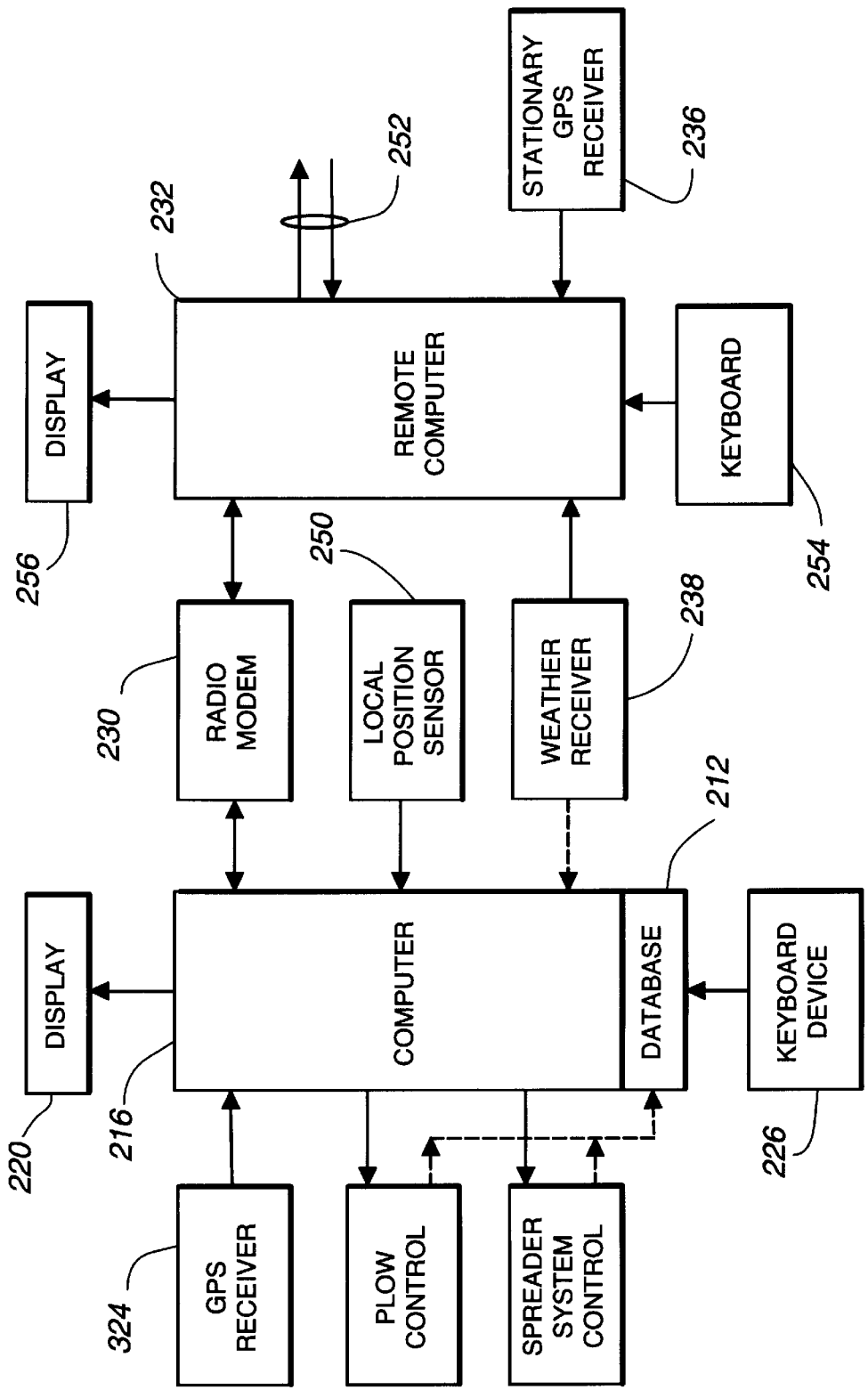
FIG. 10 is a block diagram of the automatic control system for the material spreader in accordance with the invention.

Referring now to FIGS. 9 and 10, a block diagram of a remote surface condition sensing and control apparatus in a third embodiment of the invention is shown for providing real time surface condition information to the vehicle operator and to the on board computer 216 utilized to automatically control the material spread on the vehicle roadway surface. This third embodiment is a completely automatic sensing and material application apparatus 200 which is mounted on the vehicle 40. The local sensing portion is shown in FIG. 9. The control and remote component connections are shown in FIG. 10. The sensing portion of the system 200 includes at least one electromagnetic radiation transceiver 202 which emits a ultra-wide band (UWB) impulse radar. A very short electromagnetic (EMR) impulse is propagated from transceiver 202 and echoes that reflect from the road surface 204 and from material on the road surface are evaluated. These reflected signals are set to a depth processor 206, a density processor 208, and at least a chemical composition processor 210. The EMR reflected pulse may be utilized directly by the depth processor 206 to determine the depth of any surface layer of material on the roadway. However, the density processor, and composition processors 208 and 210 rely also on input from a database 212 to determine, by comparison to peak height or phase shift of the reflected signal versus the incident signal, an output which is unique to a particular chemical composition and density. Comparing these outputs to the database content produces or can result in quantitative density and composition information 214 which is, in turn, fed to computer 216 along with depth information 218.

The depth 218 is processed in the computer 216 to provide a display 220 with information necessary to determine what additional chemicals need to be deposited on the road surface in order to minimize the hazardous conditions. In addition, the computer 216 may provide a direct output to a control device for automatically dispensing the appropriate amounts of chemicals to the road surface as the vehicle drives over the road surface.

An infrared transceiver 222 is also mounted on the vehicle and is directed toward the road surface. The transceiver 222 provides an output to a road temperature processor 224 which in turn also feeds an output to the computer 216 indicative of the actual road surface temperature.

The apparatus 200, in accordance with the third embodiment of the present invention, may be compactly designed for unitary installation in the cab of a road maintenance vehicle, such as a salt truck, with the display 220 and an input device 226 such as a keyboard integrated into the dashboard of the vehicle. The driver can then input to the computer 216 desire deicing concentrations or other desired input information. The computer 216 then can compare the actual composition and status of the material already on the road and preferably display this information for the operator to use in manually controlling application of chemicals and/or automatically control the dispensation of additional chemicals to the road surface. The automatic dispensing of chemicals may be automatically determined by the computer from a database of predetermined criteria for that location or calculated based on weather conditions, sensed road surface conditions, and the desired road surface conditions. The computer 216 also provides a running historical data input to the database 212 to track chemical application data at the particular location, whether the application be manual or automatically accomplished.

As is shown in FIG. 10, the computer 216 of the apparatus 200 also may be connected through a communication interface device such as a radio modem 230 to a remote computer/processor station 232. The apparatus preferably includes an on board Global Positioning System (GPS) receiver or a Differential Global Positioning System (DGPS) receiver 234 which provides accurate spacial position information for the vehicle 40 to the computer 216. The database 212 preferably includes a Geographical Information System (GIS) format database for the region in which the vehicle 40 is being operated. Together with the GPS coordinate information from the receiver 234 and the GIS database information in the database 212, the computer 216 constantly tracks the vehicle's position and stores sensed current road conditions as above described, in the database 212. The computer 216 then compares the position with historical weather conditions and road surface conditions that have occurred at the vehicle's location which are stored in GIS format in the database 212. This position, past and current road condition information are then preferably compared with near term weather information relayed by the remote station 232, or provided directly by an on board weather data receiver, and balanced against the preprogrammed or predetermined desired requirements for the vehicle's location. The resulting difference information is then translated to compensatory surface application composition and distribution commands fed to the spreader system 42. The information is continually updated based on the most recent data as the vehicle 40 travels along its route.

The remote station 232 may be a stationary command/control station or may actually be one or more mobile stations connected via communication links in a network of other similar computers mounted in other service vehicles. The remote station 232, if stationary, may include a DGPS receiver 236 to provide reference GPS data signals to the computer 216 for very accurate DGPS position determinations. In addition, the remote station 232 and/or computer 216 may receive weather forecast data received from other sources such as the National Weather Service or private forecasting service via receiver 238. This forecast information may be correlated and translated to the particular positional coordinates of the vehicle 40 in order to predict near term weather conditions and transmit this information to the computer 216 and also predict near term trouble spots in other locations. The computer 216 or remote computer 232 may then use this weather information in conjunction with a database or lookup table of action categories to adjust the application of chemicals to the road based on the current or predicted impending conditions in addition to application adjustments for actual real time road conditions as above described. The weather information may also be used to alert other vehicles and locations as to adverse conditions. The computer 216 preferably provides control functions which include automated control of the chemical spreader system 42 as has been described with reference to embodiments 1 and 2 above except that the proportioning controls are preferably automatically implemented rather than relying on the operator to manipulate the knobs and switches.

Figure 11:
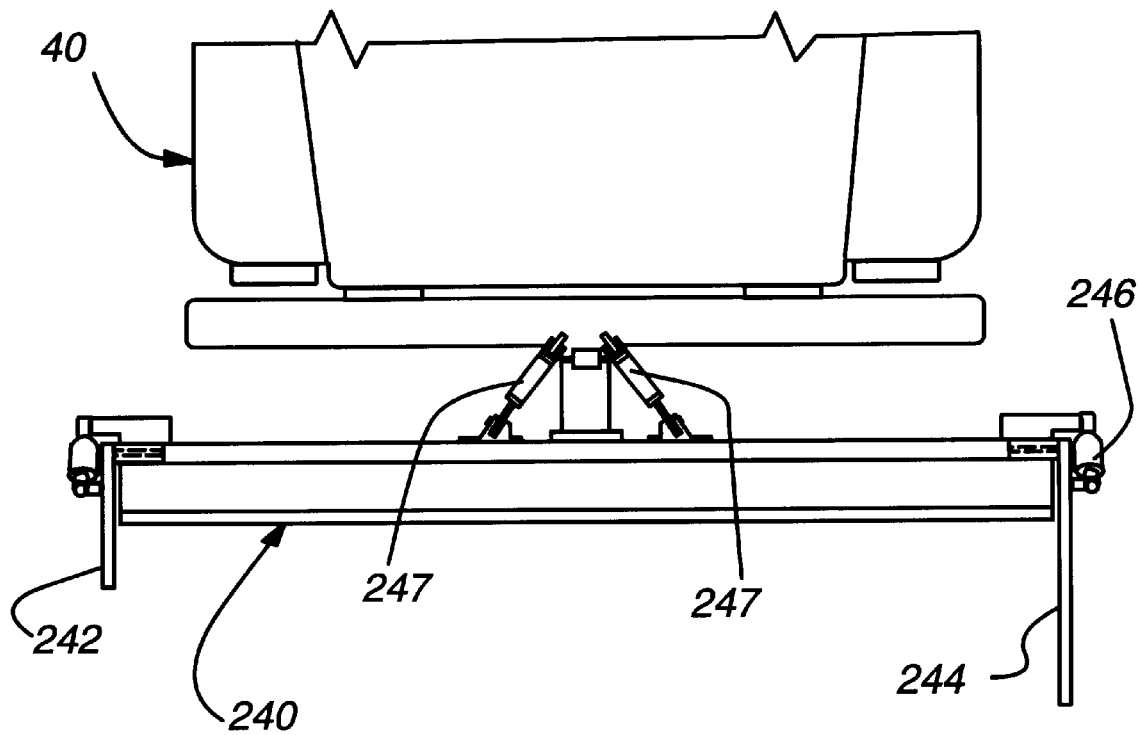
FIG. 11 is a schematic plan view of an adjustable snowplow assembly on a road service vehicle in accordance with the invention.
Figure 12:
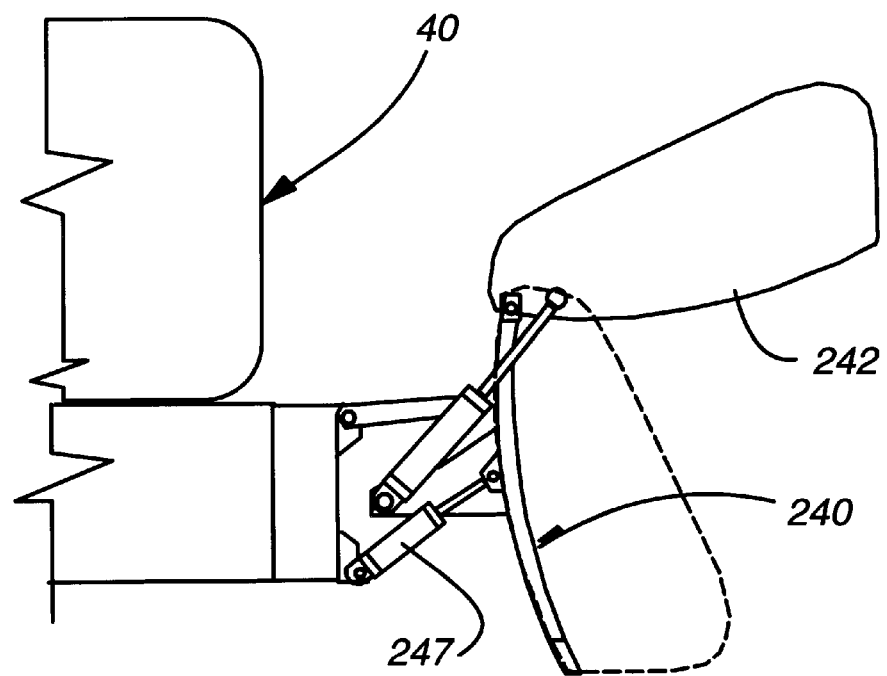
FIG. 12 is a schematic side view of the snowplow assembly shown in FIG. 11.

In addition, the computer 216 may also automatically control operation of a snow plow 240 mounted on the vehicle 40. For example, a snow plow 240, shown mounted on a vehicle 40 in a schematic plan view in FIG. 11, and in a side view in FIG. 12, may be provided that has at least one movable side discharge blocking plate 242 which is power operated, either hydraulically, electrically, or pneumatically, to raise the blocking plate 242 to permit side discharge of snow or lowered to prevent discharge of snow as the vehicle 40 passes a feature such as a residential driveway. The plow 240 may also be fitted with at least one extensible blade 244, preferably on the opposite end of the plow 240 from that carrying the blocking plate 242 which can be automatically extended or retracted in width via a hydraulic cylinder 246 depending upon the lane width at a particular location. The extensible blade 244 may be horizontally translated back and forth to extend the blade or it may be pivotally connected to the plow 240 and rotated to extend the plow path. The plow 240 may be pivoted left or right or raised and lowered by multiple cylinders 247.

The remote computer 232 may be connected to other sources of data such as other computers via a data transfer device 252. Also, to provide local input, a keyboard 254 or other input device is preferably connected to the remote computer 232. Similarly a display 256 would be provided for the operator of the remote computer 232.

Since the position of driveways, intersections, lane widths, obstructions, etc. can be included in the GIS database stored in the computer 212, and the GPS receiver can provide accurate position information for the vehicle 40, the computer 216 can be easily programmed to lower the discharge blocking plates as the vehicle passes a driveway or extend or retract the blade or change its configuration as appropriate for the lane width on a particular stretch of roadway. Alternatively, during a first pass of the vehicle 40 past a driveway, the blade may be manually extended or retracted, or blocking plates lowered and raised, and the position information sensed and fed back to the database 212 so that the computer 216 can "learn" or cause these actions to automatically be performed during future passes.

The fluid control system for the plow 240 is conventional in design. It typically will include solenoid actuated four way valves that supply and relieve hydraulic or pneumatic pressure to and from the actuating cylinders 248 for the side blocking plates 242 and the cylinder 246 for the extensible blade 244 in accordance with manual control signals from the operator or automatic signals from the computer 216.

Position markers, such as a magnetic strip, may be provided along the roadway and a local position sensor 250 such as a magnetic pickup may be mounted on the vehicle 40 to provide local sensing input for the driveway or other obstacle position to trigger movement of the blocking plates 242 or changes in the blade width or reposition the blade to avoid obstacles. These local position markers and corresponding local position sensors 250 may also be used to temporarily change the spreader discharge configuration as a driveway or obstacle is passed, rather than utilizing GPS data. It should be understood that GPS data and GIS data may be combined with use of local markers and local position sensors in a variety of combinations. For example, the use of local position markers and vehicle mounted sensors 250 may be particularly advantageously used during road construction activities to automatically override information provided by the GPS and GIS data. The computer 216 may be programmed to utilize the GPS and GIS data unless superseded by trigger of the local sensor 250 or superseding manual control by the operator.

Further, the computer 216 is preferably programmed utilizing well known decision making software techniques to compare the stored historical surface condition data and records of any remedial action previously taken during previous passes at the particular location, with current environmental forecast information, current road surface condition information, and past site specific environmental forecast data in order to predict present and future conditions at the current location. This process can be further enhanced by tracking on board the on board material contents and dispensing rates in order to predict when or if the truck 40 or an additional truck should return to the particular location. This information could then be relayed to the stationary remote location 232 or to another vehicle in the network (if the truck computers are so arranged) to forecast future service schedules.

In another, more localized application, the computer 216 can compare current road conditions through use of any of the sensing systems disclosed in U.S. Pat. No. 5,619,193 and as shown in FIG. 9 along with on board monitoring of the spreader capabilities, the fluid materials on hand, the GPS signals, and weather information received from the remote computer 232 and continually provide the operator with direction as to whether to retrace his route to make additional applications to the roadway. This automated system can thus optimize application of granular and liquid conditioning materials throughout an adverse weather pattern or storm and tailor the application based on past actions and current surface conditions. For example, in spots where unusual winds are encountered or drifting occurs, additional material applications may be required. These areas are generally predictable such that the database 212 will reflect these historical conditions therefore making the automatic control apparatus and system of the present invention particularly useful in consistently treating road surfaces in an optimum manner.

Finally, actual surface conditions and observations may also be inputted to the computer 216 via the keyboard 226 or other input device in those circumstances that are not predicted or need correction. An example of this situation might be where the traffic patterns at a particular location or along a particular route differ at different times. If the traffic is heavy, as during rush hour, more mixing on the surface of the applied chemicals and (granular materials takes place and therefore a different application mixture might be more appropriate than the computer generated amounts and proportions. If the historical data at this location involved non rush hour circumstances, the predicted requirements may need to be corrected by the operator.

The apparatus and system in accordance with the present invention has been described with reference to particular embodiments thereof. These embodiments are shown by way of examples and not by way of limitation. There are many changes, alternatives, variations, and modifications to these embodiments that will be readily apparent to those skilled in the art. For example, additional sensors may be provided to the computer 216 in order to provide more up to date local information. For example, a wind speed and direction sensor, dew point indicator and/or temperature sensor may be provided on the vehicle 40 which the computer 216 can use to modify the weather data provided by the remote computer 232 in order to tailor application of materials more exactly to local conditions and requirements. Accordingly, it is intended that all such alterations and variations and modifications to the embodiments be included within the scope of the present invention as defined by the appended claims. All patents, patent applications, and other printed publications referred to herein are hereby incorporated by reference in their entirety.

What is claimed is:

1. A synchronized-width fluid material spreading system carried by a vehicle carrying at least a triggering fluid material capable of being applied to a vehicle travel surface and at least one slave fluid material carried on said vehicle capable of being applied to said vehicle travel surface, said system comprising:
   a triggering fluid material application device supported on said vehicle and communicating with said triggering fluid material;
   at least one slave fluid material application device supported on said vehicle communicating with said slave fluid material for application of said slave fluid material to said vehicle travel surface;
   a controller coupled to said triggering fluid application device and said slave fluid application device said controller having at least one user actuatable control thereon for turning on said triggering and slave fluid material application devices and controlling a spread width of said slave material applied in response to a spread width application of said triggering fluid material on said vehicle travel surface, and
   a computer and a database connected to said computer for tracking and recording parameters indicative of the application rates of said triggering and slave materials to said vehicle travel surface, and a global positioning system receiver connected to said computer for providing location information, said computer correlating said application parameters to a position of said vehicle and recording said correlated parameters in said database.

2. The system according to claim 1 further comprising another database connected to said computer providing predetermined proportioning settings for said proportional controller related to specific geographical locations on said vehicle travel surface.

3. A travel surface conditioning vehicle comprising:
   a positionable plow mounted on and carried by the vehicle operable between a raised position and a lowered position proximate a vehicle travel surface via controls located in a cab of said vehicle;
   at least a triggering fluid material carried by the vehicle capable of being selectively applied to said vehicle travel surface;
   a triggering fluid material application device mounted on said vehicle and communicating with said triggering fluid material; and
   a fluid material spreading system for application of said triggering fluid material to said vehicle travel surface in conjunction with positioning of said plow, said system including a controller coupled to said plow controls and said triggering fluid application device, said controller having at least one user actuatable control thereon for selectively turning on said triggering material application device and controlling a spread width of application of at least said triggering material to said vehicle travel surface in response to lowering said plow to said vehicle travel surface.

4. The vehicle according to claim 3 wherein said fluid material spreading system further comprises a slave material carried on said vehicle and a slave material application device mounted on said vehicle for distributing said slave material to said vehicle travel surface.

5. The vehicle according to claim 4 wherein said controller controls operation of said slave material application device in response to actuation of said triggering material application device.

6. The vehicle according to claim 3 further comprising a computer having a database connected to said plow controller and to said spreader controller for automatically controlling application of said triggering material and positioning said plow according to a location of said vehicle.

7. The vehicle according to claim 6 wherein said material spreading system further comprises a slave material carried in a slave material container on said vehicle and a slave material application device coupled to said controller mounted on said vehicle.

8. The vehicle according to claim 7 wherein said controller operates said slave material application device in response to actuation of said triggering material application device.

9. The vehicle according to claim 6 further comprising a Global Positioning System Receiver on said vehicle connected to said computer to provide location information to said computer.

10. The vehicle according to claim 9 wherein said plow further comprises a remotely operable side discharge blocking plate operably connected to said computer for automatically positioning said blocking plate in response to location information provided to said computer by said Global Positioning System receiver.

11. A synchronized-width fluid material spreading system carried by a vehicle carrying a positionable plow, at least a triggering fluid material capable of being applied to a vehicle travel surface and at least one slave fluid material carried on said vehicle capable of being applied to said vehicle travel surface, said system comprising:
   a computer having a database, said computer being connected to said positionable plow and to a Global Positioning System receiver, said computer automatically positioning said plow in response to vehicle position at predetermined locations stored in said database;
   a triggering fluid material application device supported on said vehicle and communicating with said triggering fluid material;
   at least one slave fluid material application device supported on said vehicle communicating with said slave fluid material, and
   a controller coupled to said computer and to said triggering fluid application device and said slave fluid application device, said controller having at least one user actuatable control thereon for turning on said triggering and slave fluid material application devices and automatically controlling a rate of application and width of application of said slave material in response to application of said triggering fluid material on said vehicle travel service.

12. The system according to claim 11 wherein said computer automatically controls application of said triggering material to said vehicle surface.

13. The system according to claim 12 further comprising a geographical information system database connected to said computer for receiving and providing material application criteria from and to said computer.

14. The system according to claim 13 wherein said plow includes a discharge blocking plate that is operable under computer control, said blocking plate being lowered to block discharge from said plow as said vehicle passes a predetermined location as determined from said Global positioning system receiver and said geographical information system database.

15. The system according to claim 14 wherein said computer automatically controls application of said triggering and slave materials to said travel surface in response to discharge blocking plate position.

16. The system according to claim 15 wherein spread widths of each said triggering and slave materials is adjusted in response to said discharge blocking plate being lowered.

17. The system according to claim 16 wherein said plow further comprises an extensible extension controllable from said computer for changing blade width automatically in accordance with predetermined location criteria.

18. A travel surface conditioning vehicle comprising
   a positionable plow mounted on and carried by the vehicle operable between a raised position and a lowered position proximate a vehicle travel surface via controls located in a cab of said vehicle;
   at least a triggering fluid material carried by the vehicle capable of being selectively applied to said vehicle travel surface;
   a triggering fluid material application device mounted on said vehicle and communicating with said triggering fluid material; and
   a fluid material spreading system for application of said triggering fluid material to said vehicle travel surface in conjunction with positioning of said plow, said system including a controller coupled to said plow controls and said triggering fluid application device, said controller having at least one user actuatable control thereon for selectively turning on said triggering material application device and automatically controlling the lowering of said plow to said vehicle travel surface in response to application of at least said triggering material to said vehicle travel surface.

19. The vehicle according to claim 18 wherein said fluid material spreading system further comprises a slave material carried on said vehicle and a slave material application device mounted on said vehicle for distributing said slave material to said vehicle travel surface.

20. The vehicle according to claim 19 wherein said controller controls operation of said slave material application device in response to actuation of said triggering material application device.

21. The vehicle according to claim 18 further comprising a computer having a database connected to said plow controller and to said spreader controller for automatically controlling application of said triggering material and positioning said plow according to a location of said vehicle.

22. The vehicle according to claim 21 wherein said material spreading system further comprises a slave material carried in a slave material container on said vehicle and a slave material application device coupled to said controller mounted on said vehicle.

23. The vehicle according to claim 22 wherein said controller operates said slave material application device in response to actuation of said triggering material application device.

24. The vehicle according to claim 21 further comprising a Global Positioning System Receiver on said vehicle connected to said computer to provide location information to said computer.

25. The vehicle according to claim 24 wherein said plow further comprises a remotely operable side discharge blocking plate operably connected to said computer for automatically positioning said blocking plate in response to location information provided to said computer by said Global Positioning System receiver.

* * * * *